US007452348B2

(12) United States Patent
Hasegawa

(10) Patent No.: US 7,452,348 B2
(45) Date of Patent: Nov. 18, 2008

(54) TRANSFER NEEDLE ASSEMBLY

(75) Inventor: Mitsuru Hasegawa, Osaka (JP)

(73) Assignee: Nipro Corporation, Osaka (JP)

( * ) Notice: Subject to any disclaimer, the term of this patent is extended or adjusted under 35 U.S.C. 154(b) by 1034 days.

(21) Appl. No.: 10/733,198

(22) Filed: Dec. 11, 2003

(65) Prior Publication Data

US 2004/0122374 A1 Jun. 24, 2004

(30) Foreign Application Priority Data

Dec. 19, 2002 (JP) ............................ 2002-367640

(51) Int. Cl.
*A61B 19/00* (2006.01)
*A61M 5/32* (2006.01)

(52) U.S. Cl. ...................................................... 604/411

(58) Field of Classification Search ......... 604/403–414, 604/415, 187, 82–91; 141/382–386, 330
See application file for complete search history.

(56) References Cited

U.S. PATENT DOCUMENTS

| | | | | |
|---|---|---|---|---|
| 4,564,054 | A * | 1/1986 | Gustavsson | 141/329 |
| 4,576,211 | A | 3/1986 | Valentini et al. | 141/329 |
| 5,356,380 | A * | 10/1994 | Hoekwater et al. | 604/85 |
| 5,984,899 | A | 11/1999 | D'Alessio et al. | 604/198 |
| 6,070,623 | A | 6/2000 | Aneas | 141/329 |
| 6,159,192 | A | 12/2000 | Fowles et al. | 604/403 |
| 6,171,293 | B1 * | 1/2001 | Rowley et al. | 604/403 |
| 6,358,236 | B1 | 3/2002 | DeFoggi et al. | 604/414 |
| 6,378,714 | B1 | 4/2002 | Jansen et al. | 215/249 |
| 6,551,299 | B2 | 4/2003 | Miyoshi et al. | 604/403 |
| 2001/0025671 | A1 | 10/2001 | Safabash | 141/329 |

FOREIGN PATENT DOCUMENTS

| | | | |
|---|---|---|---|
| EP | 0 126 718 | A2 | 11/1984 |
| EP | 0 311 787 | A2 | 4/1989 |
| JP | 5-277156 | A | 10/1993 |
| JP | 7-213585 | A | 8/1995 |
| JP | 10-277154 | A | 10/1998 |
| JP | 10-323389 | A | 12/1998 |
| JP | 2001-321416 | A | 11/2001 |
| JP | 2002-172151 | A | 6/2002 |

* cited by examiner

*Primary Examiner*—Matthew F Desanto
(74) *Attorney, Agent, or Firm*—Kubovcik & Kubovcik

(57) ABSTRACT

A transfer needle assembly including a cap-like outside guide member; a tubular inside guide member; and a puncture member. The puncture member has a tip fitting portion at a proximal end and a puncture needle at a distal end. The inside guide member can slide along an inner wall of a skirt portion of the outside guide member from a position where a distal end of the needle is receded in the inside guide member, to a position where the distal end of the needle projects outside of the inside guide member. At the position where the distal end of the needle is receded in the inside guide member, the outside guide member and the inside guide member are engaged so as to be incapable of sliding, with the engagement being releasable by inserting a mouth portion of a vial into the inside guide member.

25 Claims, 9 Drawing Sheets

31
TN
42
32
4

122
24
22
2

TN
32
41
4

24
122
2

TN
1
32
2
4

TRANSFER NEEDLE ASSEMBLY

BACKGROUND OF THE INVENTION

1. Field of the Invention

The present invention relates to a transfer needle assembly. The transfer needle assembly of the present invention eliminates problems such as the contamination of the tip of a needle before use and an injury by the tip of a needle and the leakage of a liquid when in use.

2. Description of the Related Art

For the preparation of a component liquid to be applied to a living body and mixed and injected at a medical facility or self-injected for home medical treatment, a dried medicine contained in a vial is dissolved, prepared and then transferred to a syringe to be used. A syringe with a needle or a tool having a hollow puncture needle at both ends, called a “double-ended needle”, has been used for these operations. When the syringe with a needle is used, a rubber stopper in the mouth portion of a solution container is pricked with the needle to collect a predetermined amount of the solution into the syringe and then a rubber stopper in the mouth portion of a vial is pricked with the needle to inject the solution into the vial. Then the vial is shaken to dissolve the medicine and the rubber stopper is pricked with the needle again to collect a predetermined amount of the medicinal liquid into the syringe. Further, when the double-ended needle is used, the rubber stopper of a vial filled with a medicine and the rubber stopper of a solution container are pricked with the puncture needles at both ends of the double-ended needle to provide communication between them, the solution is transferred to the vial to dissolve the medicine, the solution container and the double-ended needle are removed from the vial, and the rubber stopper of the vial is pricked with the needle likewise to collect a predetermined amount of the medicinal liquid into the syringe.

These prior art techniques involve a problem in that when the operation of dissolving a medicine is carried out using the syringe with a needle, the operation is complicated, the tip of the needle may become contaminated before use as the needle is exposed, and a patient or the like may be injured by the tip of the needle when in use. Further, when the double-ended needle is used and the needle is pulled out or a predetermined amount of the medicinal liquid is collected into the syringe, a patient or the like may be injured by the tip of the needle and the tip of the needle may be contaminated before the collection of the medicinal liquid because the tip of the needle is exposed the same as with the syringe with a needle. To solve the above problems, there is proposed an admixture injection adaptor which enables the injection and collection of a medicinal liquid during a dissolution operation (see Japanese laid open publication No. JP 7-213585).

In the admixture injection adaptor of the above JP 2002-360593 A, a hollow puncture needle and a pipe-shaped tip fitting part are set on opposite sides on the axis of a disc hub, respectively, and on the outer edge of the hub, tubular skirts concentrically extending over the puncture needle and the tip fitting part are constructed. The adaptor is convenient when it is used to transfer a medicinal liquid in a vial to a syringe after a dried medicine in the vial is dissolved to prepare the medicinal liquid because contamination of the tip of the needle or an injury by the needle is avoided. However, the length of the skirt is limited to prevent the end of the skirt from contacting with the shoulder of the vial when the vial is pricked with the needle, whereby the vial cannot be fitted straight, thereby forming a gap between the rubber stopper of the vial and the needle and thereby causing leakage of the medicinal liquid during the dissolution operation.

The present invention has been made in view of the above circumstances, and it is, therefore, an object of the present invention to provide a transfer needle assembly with which the dissolution operation can be carried out easily; contamination of the tip of the needle and injury by the tip of the needle can be avoided; and leakage of a liquid during the dissolution operation can be prevented.

BRIEF SUMMARY OF THE INVENTION

From results of extensive studies, the inventors of the present invention have conceived of providing a two-position structure to a vial guide portion in order to solve the problems described above, thus arriving at the present invention. That is, at a stage before use, a needle tip is housed in an inside vial guide portion, and the inside vial guide portion is caused to retract when piercing a needle tip into a rubber stopper.

That is, the present invention relates to the following assemblies.

(1) A transfer needle assembly comprising:

a cap-like outside guide member having a top surface and a skirt portion;

a tubular inside guide member that is inserted into the outside guide member; and a puncture member which passes through the top surface of the outside guide member, wherein:

the puncture member is a tubular member having at its proximal end a tip fitting portion for fitting a syringe tip and having at its distal end a puncture needle;

the puncture needle is provided with a liquid passage;

the liquid passage communicates with the tip fitting portion;

the inside guide member is capable of sliding along an inner wall of the skirt portion of the outside guide member from a position where a distal end of the puncture needle is receded in an inside of the inside guide member, to a position where the distal end of the puncture needle projects outside of the inside guide member;

at the position where the distal end of the puncture needle is receded in the inside of the inside guide member, the outside guide member and the inside guide member are releasably engaged with each other so as to be incapable of sliding; and the engagement between the outside guide member and the inside guide member is releasable by inserting a mouth portion of a vial into the inside guide member.

(2) A transfer needle assembly according to (1) above, wherein the skirt portion of the outside guide member includes:

an annular projection provided in an inner wall of a distal end of the skirt portion;

a plurality of axially extending slits formed in a portion on a proximal end side, with respect to the annular projection, of the skirt portion; and a plurality of flexible engaging claws formed between pairs of the plurality of slits, the plurality of flexible engaging claws inclining toward an inside in a distal end direction, wherein a proximal end side of the inside guide member includes:

an annular projection provided in an outer wall of a proximal end;

a plurality of axially extending slits formed in a proximal end portion of the inside guide member corresponding to the plurality of engaging claws; and a plurality of flexible pushing claws formed between pairs of the plurality of slits, the plurality of flexible pushing claws inclining toward an inside of the inside guide member in a proximal end direction, and wherein, at the position where the distal end of the puncture needle is receded in the inside of the inside guide member, the engaging claws and the proximal end of the inside guide member are engaged with each other and the annular projection of the outside guide member and the annular projection of the inside guide member are engaged with each other, and by inserting the mouth portion of the vial into the inside guide member, the pushing claws push the engaging claws to the outside, causing the engaging claws to deform and release the engagement between the outside guide member and the inside guide member.

(3) A transfer needle assembly according to (1) or (2) above, wherein the puncture member is formed integrally with the outside guide member.

(4) A transfer needle assembly according to (1) or (2) above, comprising a puncture needle insertion portion axially provided in the top surface of the outside guide member and having an opening that passes through the top surface, wherein the puncture member is provided separately from the outside guide member and is inserted into the opening of the puncture needle insertion portion.

(5) A transfer needle assembly according to any one of (1) to (4) above, comprising a plurality of vertical ribs provided in an inner wall of the inside guide member.

(6) A transfer needle assembly according to any one of (1) to (5) above, comprising a collar formed at the distal end of the skirt portion of the outside guide member, the collar inclining to the outside in the distal end direction.

It should be noted that the terms "proximal end" and "distal end" as used herein refer to an upper end and a lower end, respectively, as in FIG. 3.

DETAILED DESCRIPTION OF THE INVENTION

Figure 1:
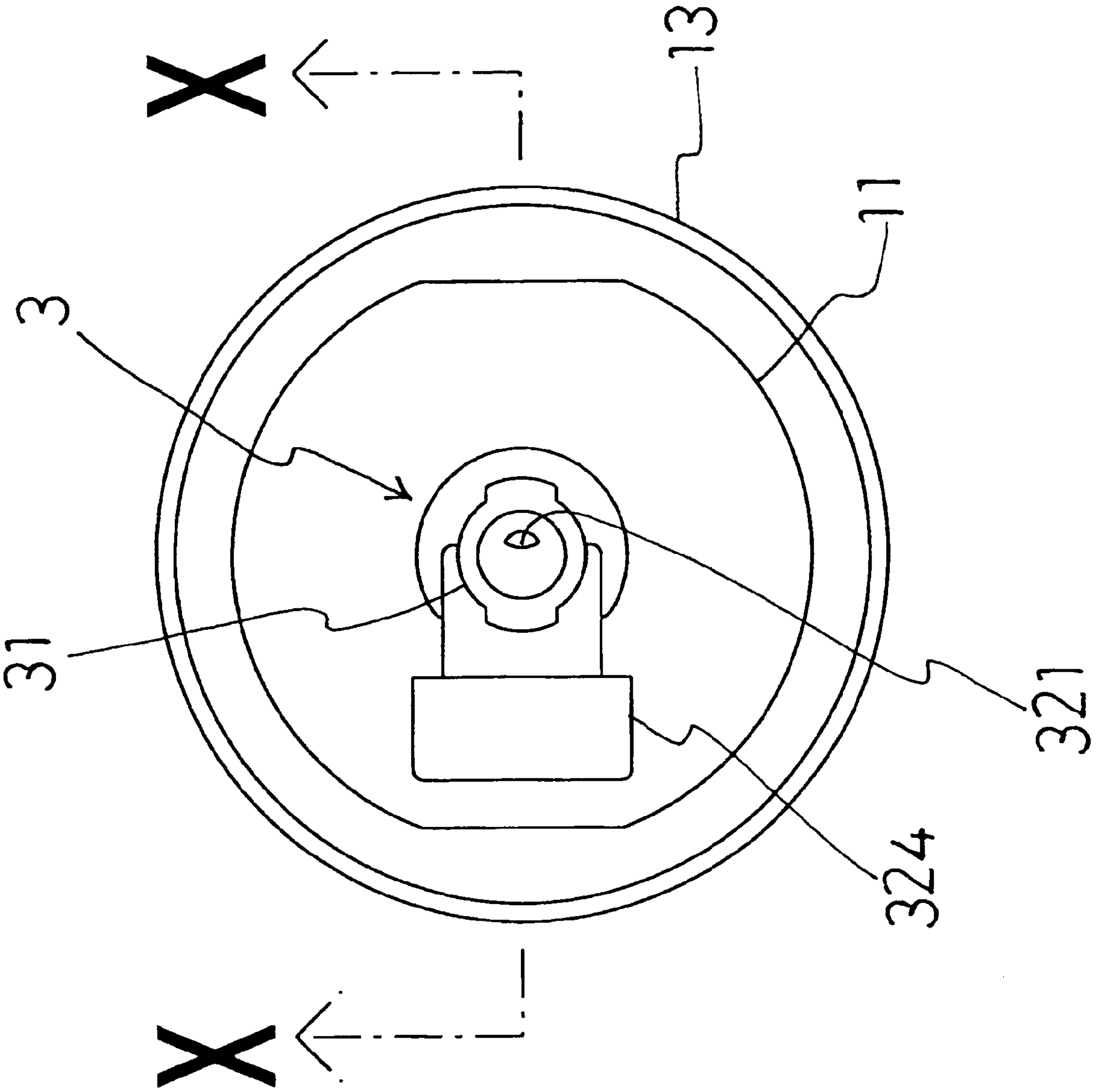
FIG. 1 is a plan view showing an embodiment of the present invention.

As shown in FIGS. 1 to 5, the transfer needle assembly according to the present invention includes a cap-like outside guide member 1, a tubular inside guide member 2, and a puncture member 3. The puncture member 3 is a tubular member having a tip fitting portion 31 at its proximal end and a puncture needle 32 at its distal end. The puncture needle 32 is provided with a gas passage 322 which is provided with an air filter 33 in an opening portion 324 and a liquid passage 321 which communicates with the tip insertion portion 31. Further, the inside guide member 2 is capable of sliding along an inner wall of a skirt portion 12 of the outside guide member 1 from a position where a distal end of the puncture needle 32 is receded in the inside of the inside guide member 2, to a position where the distal end of the puncture needle 32 projects outside of the inside guide member 2. The outside guide member 1 and the inside guide member 2 are releasably engaged with each other in the position where the distal end of the puncture needle 32 is receded in the inside of the inside guide member 2, so as to be incapable of sliding; and the engagement between the outside guide member 1 and the inside guide member 2 is releasable by inserting a mouth portion of a vial into the inside guide member 2.

The outside guide member 1 is a cap-like member that is normally formed from a flexible resin such as polypropylene, polyethylene, polyester, polyvinyl chloride, or ABS resin. The outside guide member 1 has a top surface 11 and a tubular skirt portion 12. The inside guide portion 2 is inserted into the skirt portion 12, and the puncture member 3 is provided in the top surface 11, passing through the top surface 11.

When the inside guide member 2 is gripped by hand, the hand may get in the way and it becomes difficult to slide the inside guide member 2. A collar 13 having a funnel shape, for example, which inclines to the outside in a distal end direction may also be provided in the distal end of the skirt portion 12 of the outside guide member 1 in such a manner that the inside guide member 2 is not gripped during vial insertion.

The inside guide member 2 is a tubular member that is formed from a material similar to that used for the outside guide member 1. The inside guide member 2 has an outer diameter that is slightly smaller than the inner diameter of the skirt portion 12 so that it is possible for the inside guide member 2 to slide along an inner wall of the skirt portion 12 of the outside guide member 1.

The outside guide member 1 and the inside guide member 2 are releasably engaged in the position where a tip of the puncture needle 32 is receded in the inside of the inside guide member 2 so as to be incapable of sliding with respect to each other before use. This engagement can be released by inserting a mouth portion 41 of a vial 4 (refer to FIG. 9*b*) into the inside guide member 2. When the engagement between the outside guide member 1 and the inside guide member 2 is released, it becomes possible to slide the inside guide member 2 along the inner wall of the skirt portion 12 of the outside guide member 1, from a position where the tip portion of the puncture needle 32 is receded, or recessed, in the inside guide member 2 to a position where the puncture needle 32 projects to the outside.

Figure 4:
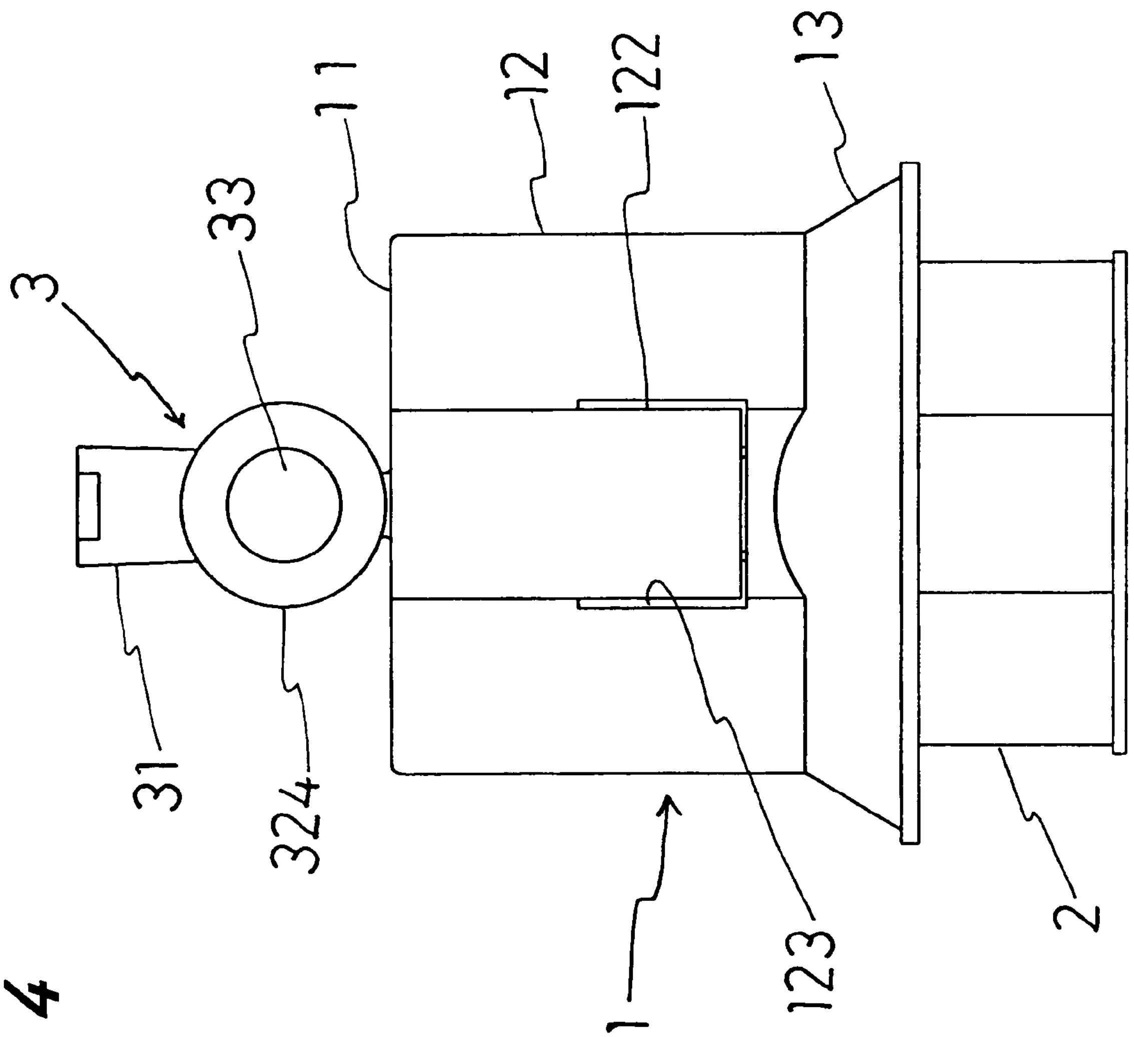
FIG. 4 is a left side view of FIG. 1.
Figure 5:
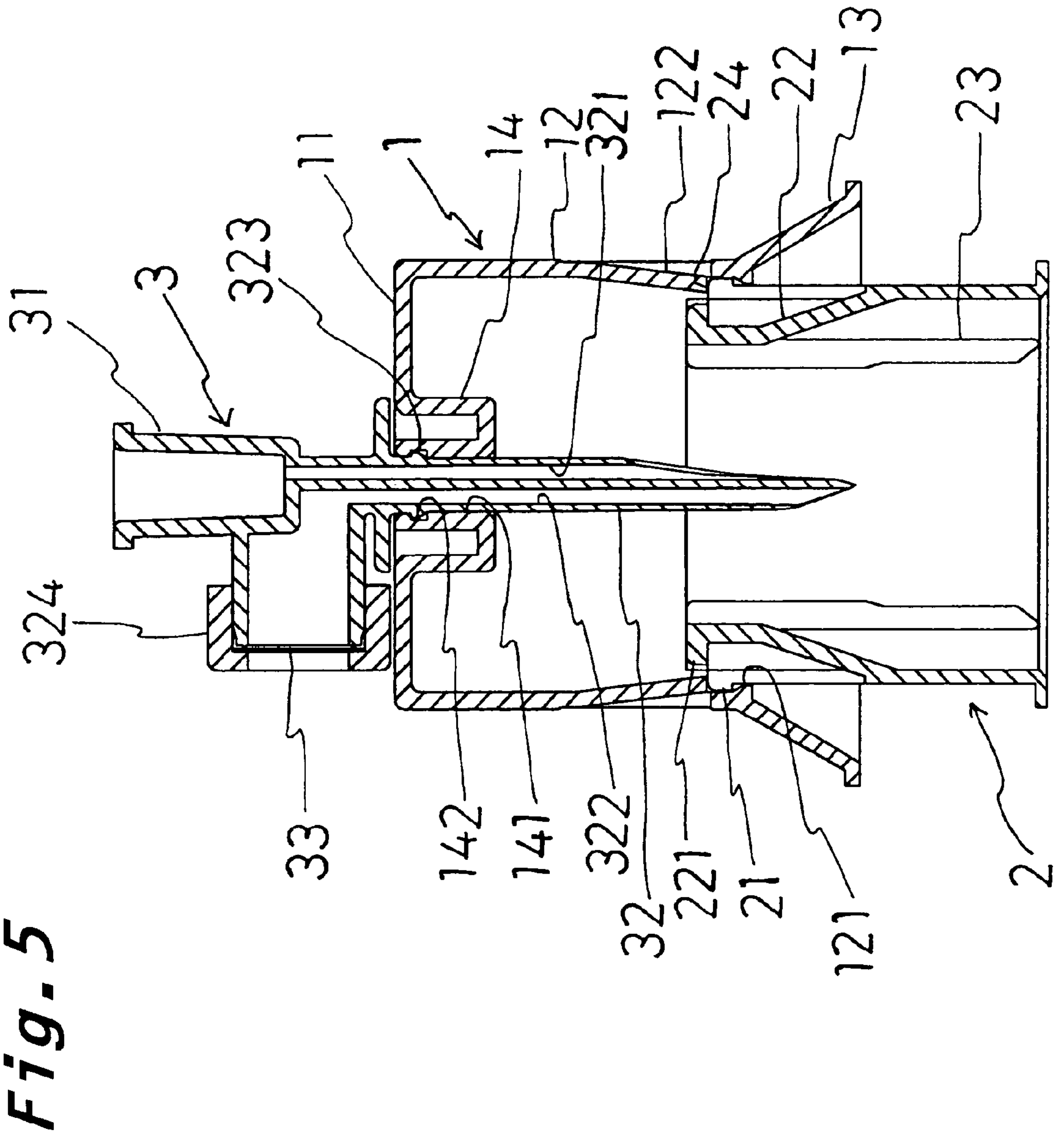
FIG. 5 is a cross sectional view of FIG. 1 along line X-X.
Figure 8:
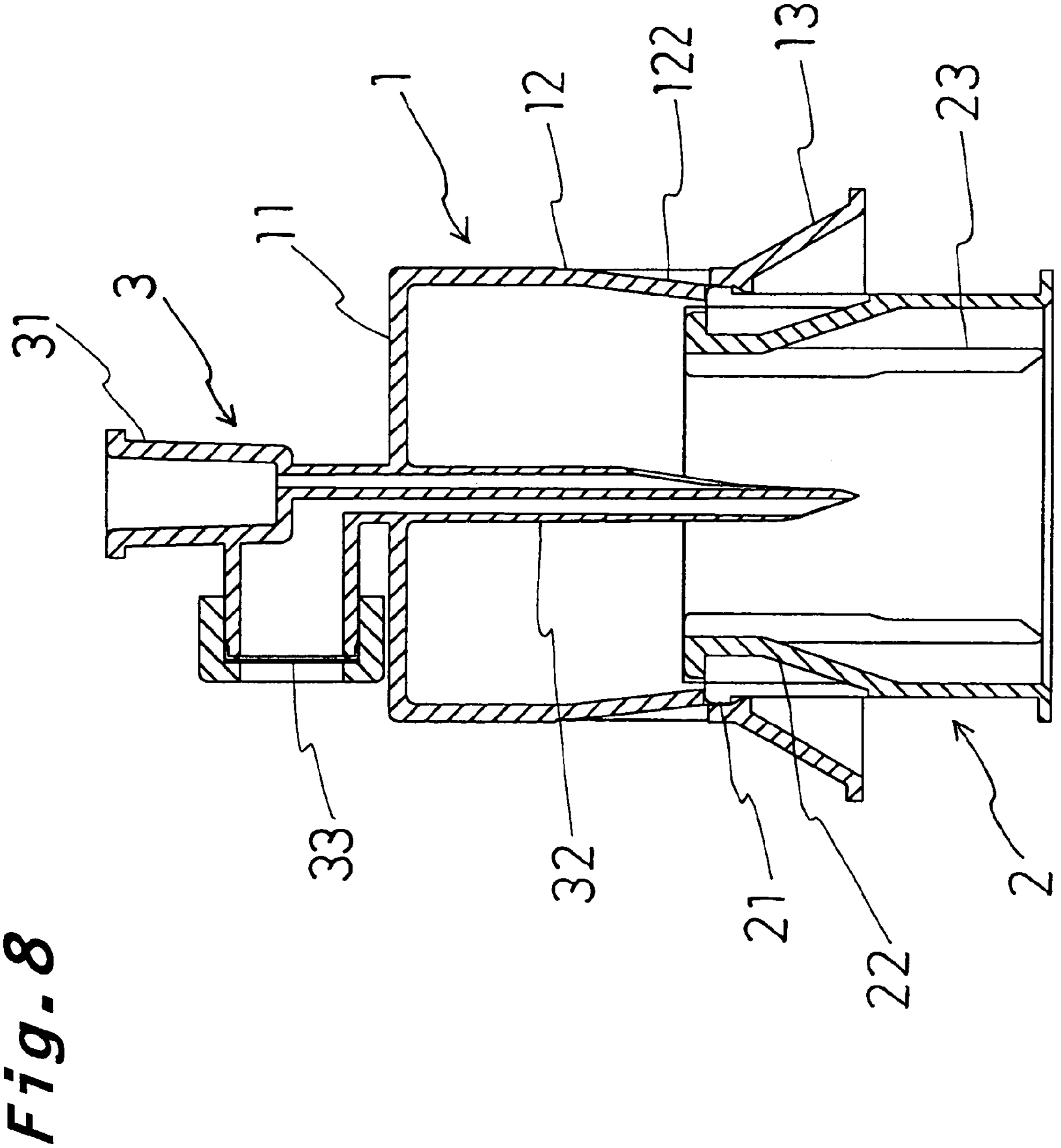
FIG. 8 is a cross sectional view that is similar to FIG. 5, showing another embodiment of the present invention.

The engagement between the outside guide member 1 and the inside guide member 2 as described above is, for example, structured as shown in FIGS. 5 and 8. That is, in the outside guide member 1, an annular projection 121 is provided in an inner wall of a distal end of the skirt portion 12, a plurality of slits 123 extending substantially in the axial direction of the outside guide member (refer to FIG. 4) are formed in a portion of the proximal end side, with respect to this annular projection 121, of the skirt portion 12, and a plurality of flexible engaging claws 122 that incline toward the inside in a distal end direction are formed by pairs of slits 123 (as best shown in FIG. 4).

Figure 6:
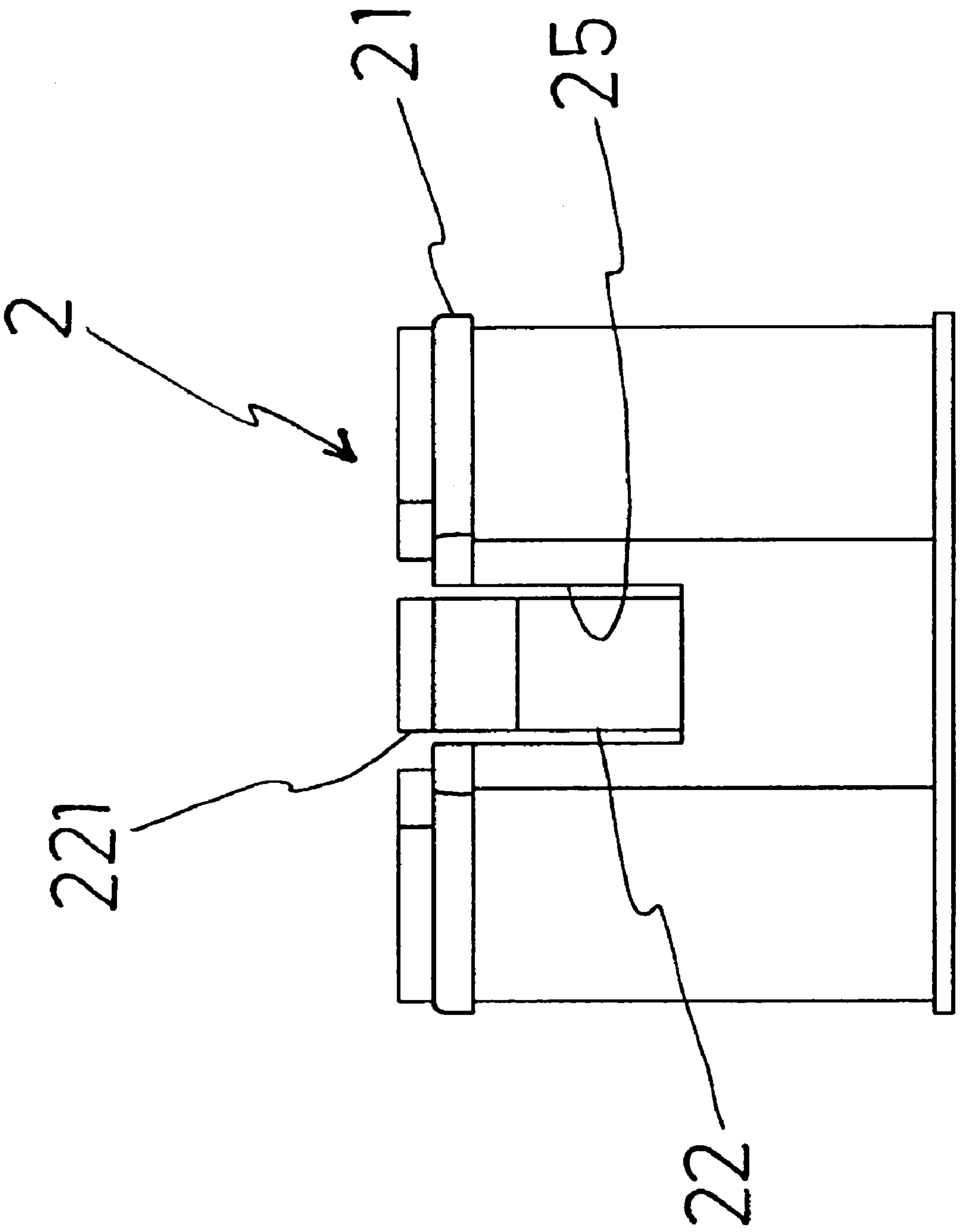
FIG. 6 is a left side view of an inside guide member that is shown in FIG. 1.
Figure 7:
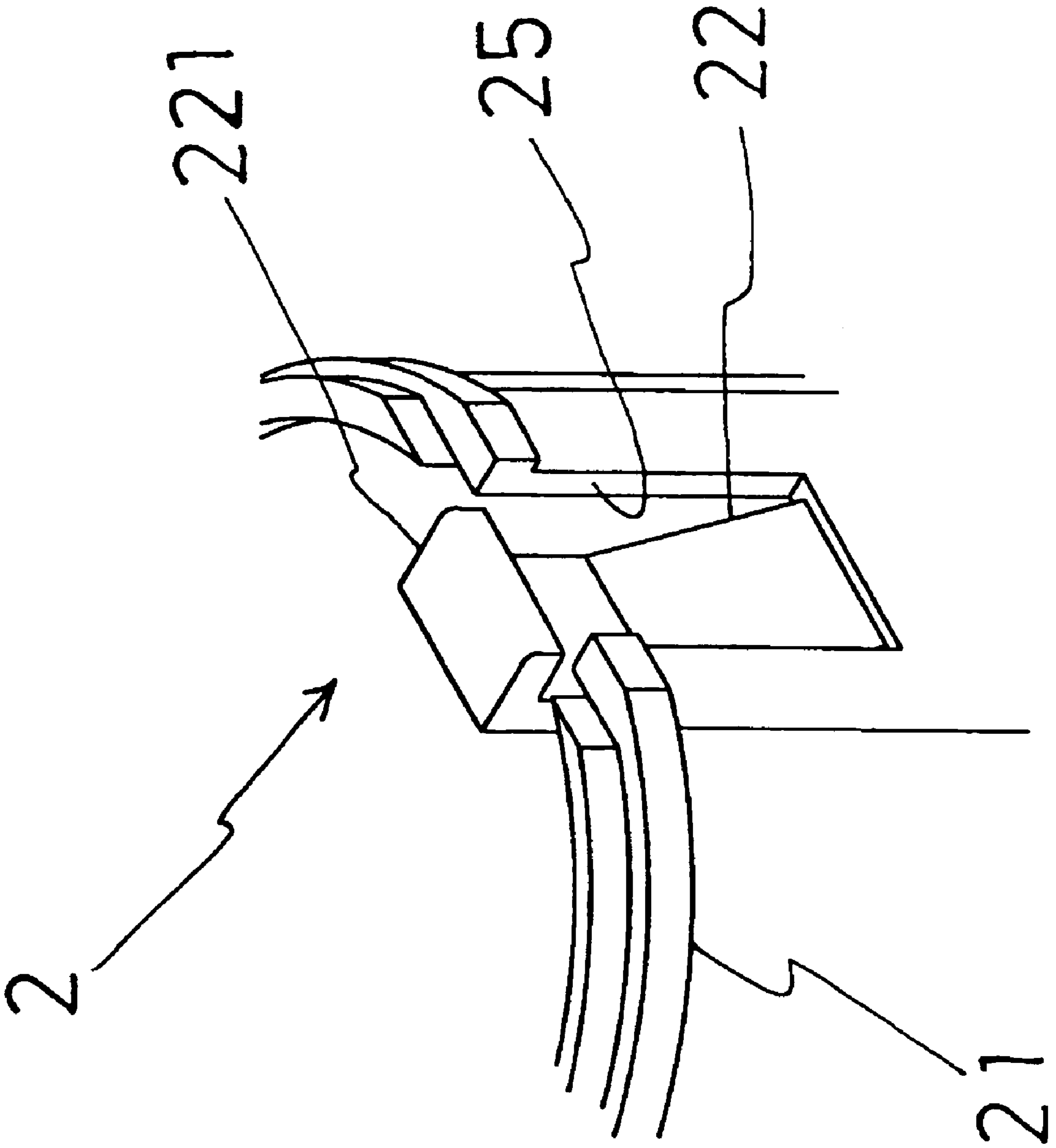
FIG. 7 is a perspective view of a main portion of the inside guide member that is shown in FIG. 1.

In the inside guide member 2, on its proximal end side, an annular projection 21 is provided in an outer wall of its proximal end as shown in FIGS. 6 and 7. A plurality of slits 25 extending substantially in the axial direction of the inside guide member (refer to FIG. 6) are formed in the proximal end portion at positions corresponding to the engaging claws 122, and a plurality of flexible pushing claws 22 that incline toward the inside of inside guide member 2 in a proximal end direction are formed between pairs of the slits 25. Before use, in the position where the distal end of the puncture needle 3 is receded in the inside of the inside guide member 2, the engaging claws 122 engage (in the sense of collide with), or abut against, the proximal end 24 of the inside guide member 2 and the annular projection 121 of the outside guide member 1 engages the annular projection 21 of the inside guide member 2. By inserting the mouth portion 41 of the vial 4 into the inside guide member 2, the pushing claws 22 are deformed to bend outward, and the outwardly bent pushing claws 22 push the engaging claws 122 to the outside, thereby releasing the engagement between the outside guide member 1 and the inside guide member 2. It should be noted that reference numeral 221 denotes a pushing portion of the pushing claw 22. The pushing portion is formed projecting to the outside so as to be situated at a height where it reliably releases the engagement between the engaging claw 122 and the proximal end 24 of the inside guide member 2 when the vial mouth portion 41 is inserted into the inside guide member 2.

A plurality of vertical ribs 23 may also be provided in the inside guide member 2 so that the vial 4 slides more easily along the inner wall of the inside guide member 2.

Figure 2:
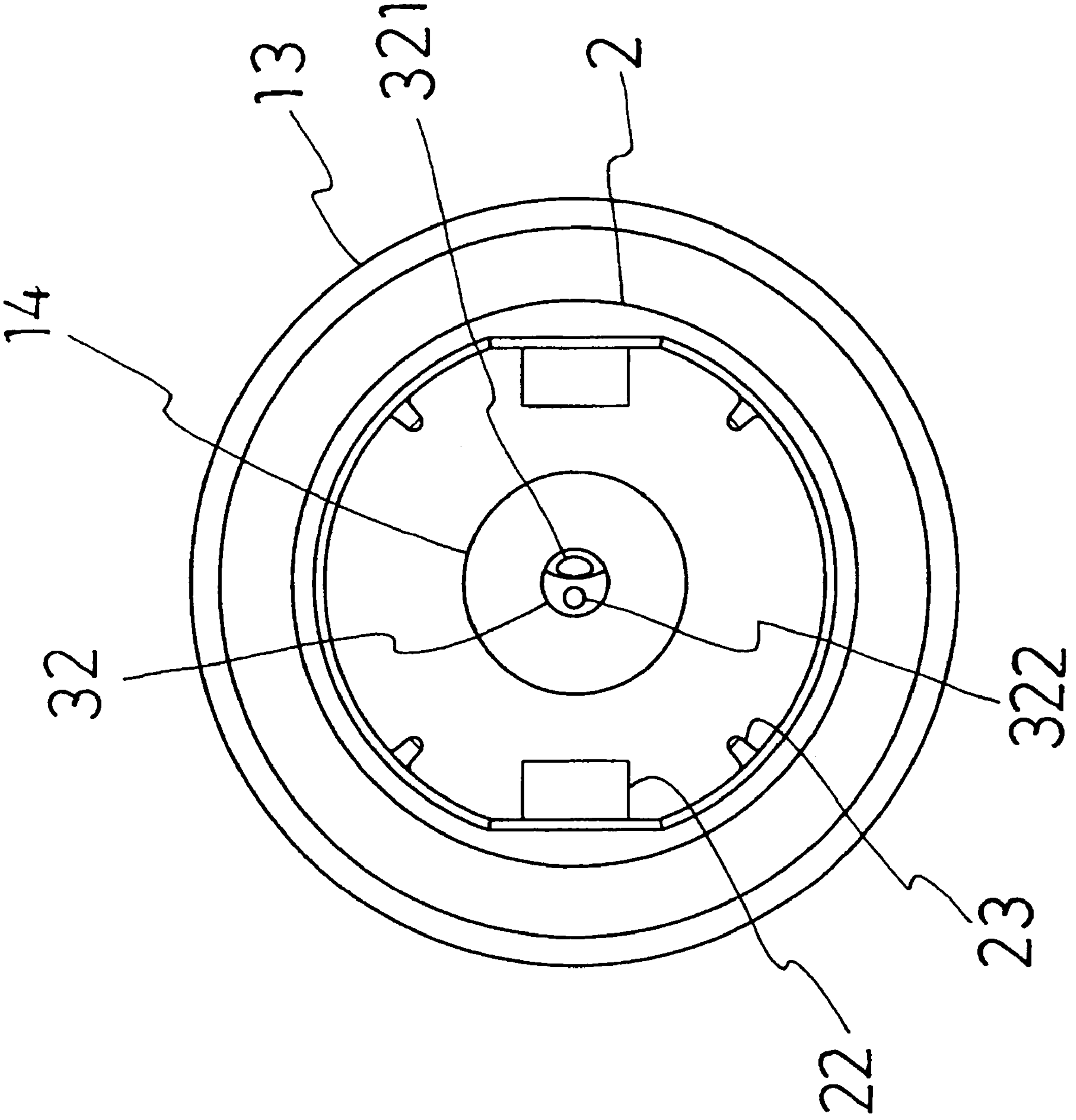
FIG. 2 is a base view of FIG. 1.
Figure 3:
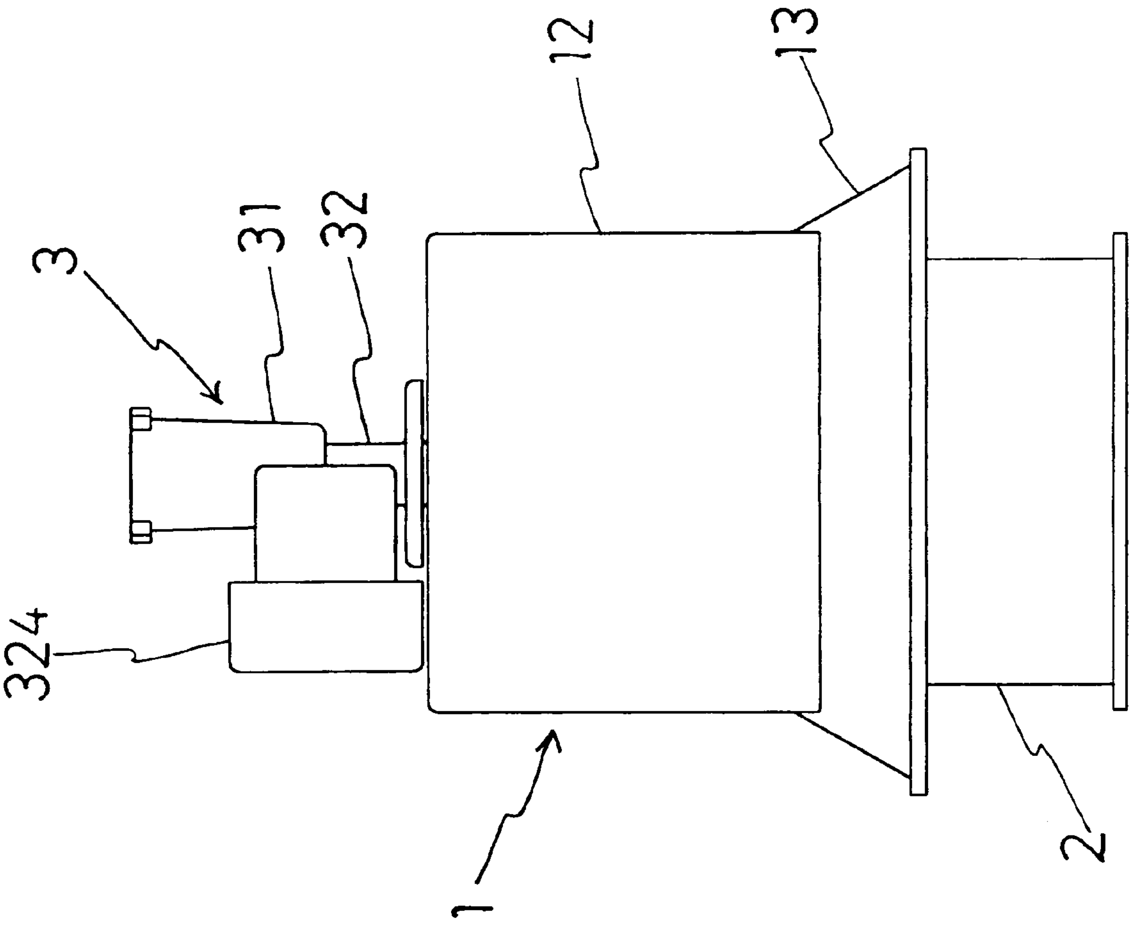
FIG. 3 is a front view of FIG. 1.

The puncture member 3 may be formed integrally with the outside guide member 1 as shown in FIG. 8, and may also be provided separately from the outside guide member 1 as shown in FIG. 5. When the puncture member 3 is provided separately from the outside guide member 1, a puncture needle insertion portion 14 having a hole, or opening, 141 that passes through the top surface 11 may be formed axially in the top surface 11 of the outside guide member 1 as shown in FIG. 2, for example. The puncture needle 32 of the puncture portion 3, which is formed separately from the outside guide member 1, may be inserted into the hole 141 of the puncture needle insertion portion 14. It should be noted that an annular groove 142 may also be formed in the inner wall of opening 141, engaging with an annular projection 323 that is formed in an outer wall of the puncture needle 32 so that the puncture member 3 does not fall off from the puncture needle insertion portion 14 during use.

Figures 9A, 9B, 9C, 9D, 9E:
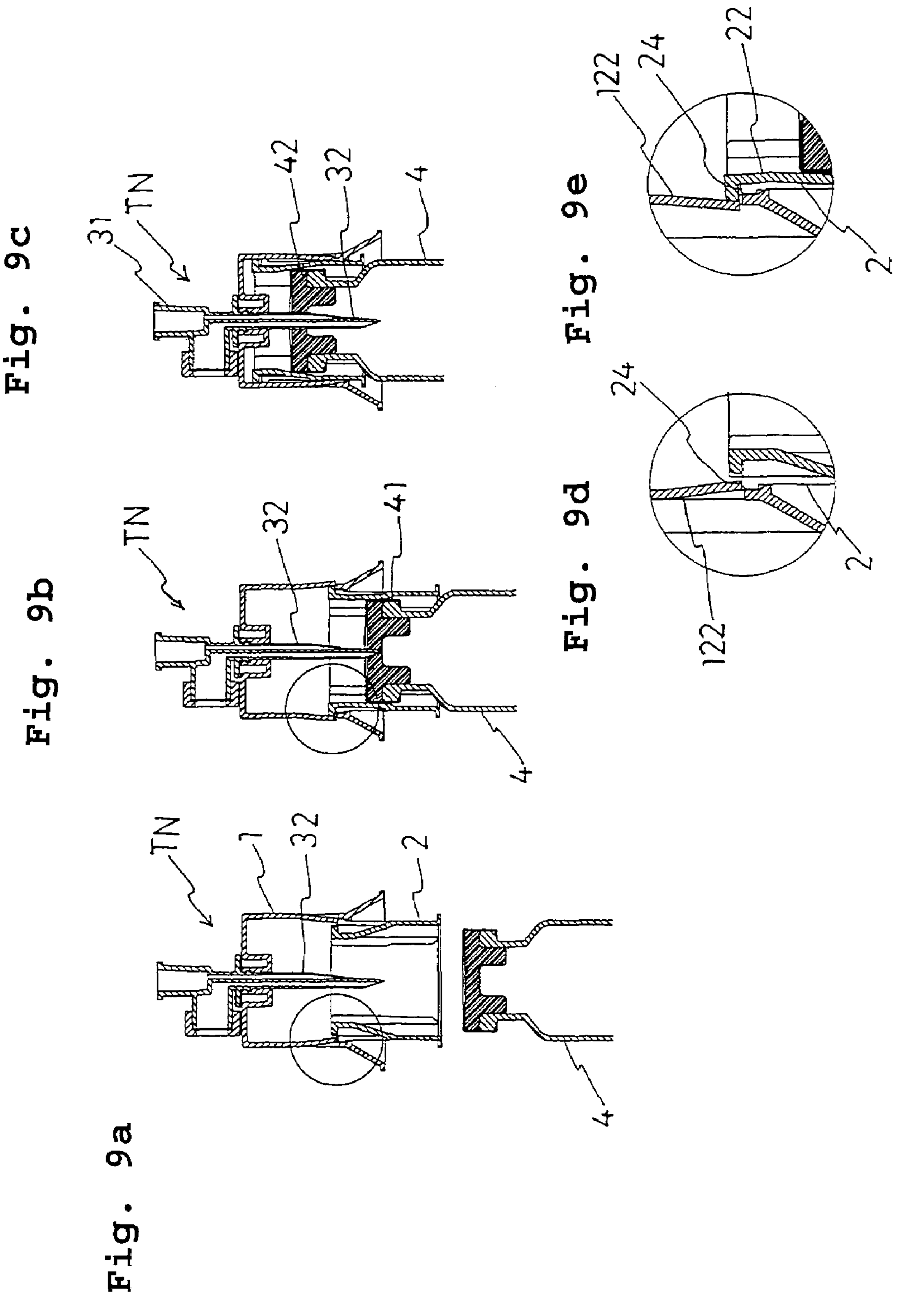
FIGS. 9(*a*)-9(*e*) are views for explaining how a transfer needle assembly according to the present invention is used.

Use of the transfer needle assembly of the present invention is explained next using FIG. 9. First, a transfer needle assembly TN like that shown in FIG. 5 is prepared (FIG. 9*a*). The engaging claw 122 of the outside guide member 1 is engaged with the proximal end 24 of the inside guide member 2 at this point (FIG. 9*d*). Next, the mouth portion 41 of the vial 4 is inserted into the transfer needle assembly TN. The transfer needle assembly TN is pushed forward to a position where the mouth portion 41 of the vial 4 pushes the pushing claw 22 of the inside guide member 2 and deflects the pushing claw 22 to the outside (FIG. 9*b*). At this point, the engaging claw 122 is pushed on and deflects to the outside by the pushing claw 22 that has been deflected to the outside. The engagement between the engaging claw 122 and the proximal end 24 of the inside guide member 2 is thus released (FIG. 9*e*). When the transfer needle assembly TN is pushed further forward, a rubber stopper 42 of the mouth portion 41 of the vial is pricked by the puncture needle 32 of the puncture member 3, and the inside of the vial 4 communicates with the outside through the transfer needle assembly TN (FIG. 9*c*). If a syringe tip (not shown) is fitted onto the tip fitting portion 31 in this state, a solution or the like filled into the syringe in advance can be injected into the vial. Further, a medical liquid after dissolution can be aspirated from within the vial 4 into the syringe.

As is apparent from the description above, the inside of a vial can be communicated with the outside simply by a hand pushing operation when employing the present invention, and therefore dissolution operations are easy. Further, the needle tip of the transfer needle assembly is receded in the inside of the inside guide member before use, and therefore contamination of the needle tip, and injuries caused by the needle tip, can be avoided when performing dissolution operations. Furthermore, the puncture needle can prick right through a center portion of the rubber stopper of a vial due to the inside guide member, and therefore liquid leakage during dissolution operations can be prevented.

What is claimed is:

1. A transfer needle assembly comprising:

a cap-like outside guide member having a top surface and a skirt portion;

a tubular inside guide member that is positioned in the outside guide member; and a puncture member which passes through the top surface of the outside guide member and has a proximal end and a distal end, wherein:

the puncture member is a tubular member having at its proximal end a tip fitting portion for fitting a syringe tip and having at its distal end a puncture needle;

the puncture needle is provided with a liquid passage;

the liquid passage communicates with the tip fitting portion;

the inside guide member is capable of sliding along an inner wall of the skirt portion of the outside guide member from a position where a distal end of the puncture needle is receded in an inside of the inside guide member, to a position where the distal end of the puncture needle projects outside of the inside guide member;

in the position where the distal end of the puncture needle is receded in the inside of the inside guide member, the outside guide member and the inside guide member are releasably engaged with each other so as to be incapable of sliding; and the engagement between the outside guide member and the inside guide member is released by insertion of a mouth portion of a vial into the inside guide member.

2. A transfer needle assembly according to claim 1, wherein the skirt portion of the outside guide member includes:

an annular projection provided in an inner wall of a distal end of the skirt portion;

a plurality of slits extending in an axial direction of the outside guide member formed in a portion of the skit portion on a proximal end side with respect to the annular projection; and a plurality of flexible engaging claws formed between pairs of the plurality of slits, the plurality of flexible engaging claws inclining toward an inside of the outside guide member in a distal end direction, wherein a proximal end side of the inside guide member includes:

an annular projection provided in an outer wall of a proximal end;

a plurality of slits extending in an axial direction of the inside guide member formed in a proximal end portion of the inside guide member corresponding to the plurality of engaging claws; and a plurality of flexible pushing claws formed between pairs of the plurality of slits, the plurality of flexible pushing claws inclining toward an inside of the inside guide member in a proximal end direction, and wherein, at the position where the distal end of the puncture needle is receded in the inside of the inside guide member, the engaging claws and the proximal end of the inside guide member are engaged with each other and the annular projection of the outside guide member and the annular projection of the inside guide member are engaged with each other, and by inserting the mouth portion of the vial into the inside guide member, the pushing claws push the engaging claws to the outside, causing the engaging claws to deform and release the engagement between the outside guide member and the inside guide member.

3. A transfer needle assembly according to claim 2, wherein the puncture member is formed, integrally with the outside guide member.

4. A transfer needle assembly according to claim 3, comprising a plurality of vertical ribs provided in an inner wall of the inside guide member.

5. A transfer needle assembly according to claim 4, comprising a collar formed in the distal end of the skirt portion of the outside guide member, the collar inclining to the outside in the distal end direction of the outside guide member.

6. A transfer needle assembly according to claim 3, comprising a collar formed in the distal end of the skirt portion of the outside guide member, the collar inclining to the outside in the distal end direction of the outside guide member.

7. A transfer needle assembly according to claim 2, comprising a puncture needle insertion portion axially provided in the top surface of the outside guide member and having an opening that passes through the top surface, wherein the puncture member is provided separately from the outside guide member and is inserted into the opening of the puncture needle insertion portion.

8. A transfer needle assembly according to claim 7, comprising a plurality of vertical ribs provided in an inner wall of the inside guide member.

9. A transfer needle assembly according to claim 8, comprising a collar formed in the distal end of the skirt portion of the outside guide member, the collar inclining to the outside in the distal end direction of the outside guide member.

10. A transfer needle assembly according to claim 7, comprising a collar formed in the distal end of the skirt portion of the outside guide member, the collar inclining to the outside in the distal end direction of the outside guide member.

11. A transfer needle assembly according to claim 2, comprising a plurality of vertical ribs provided in an inner wall of the inside guide member.

12. A transfer needle assembly according to claim 4, comprising a collar formed in the distal end of the skirt portion of the outside guide member, the collar inclining to the outside in the distal end direction of the outside guide member.

13. A transfer needle assembly according to claim 2, comprising a collar formed in the distal end of the skirt portion of the outside guide member, the collar inclining to the outside in the distal end direction of the outside guide member.

14. A transfer needle assembly according to claim 1, wherein the puncture member is formed integrally with the outside guide member.

15. The transfer needle assembly according to claim 14, comprising a plurality of vertical ribs provided in an inner wall of the inside guide member.

16. A transfer needle assembly according to claim 15, comprising a collar formed in the distal end of the skirt portion of the outside guide member, the collar inclining to the outside in the distal end direction of the outside guide member.

17. A transfer needle assembly according to claim 14, comprising a collar formed in the distal end of the skirt portion of the outside guide member, the collar inclining to the outside in the distal end direction of the outside guide member.

18. A transfer needle assembly according to claim 1, comprising a puncture needle insertion portion axially provided in the top surface of the outside guide member and having an opening that passes through the top surface, wherein the puncture member is provided separately from the outside guide member and is inserted into the opening of the puncture needle insertion portion.

19. A transfer needle assembly according to claim 18, comprising a plurality of vertical ribs provided in an inner wall of the inside guide member.

20. A transfer needle assembly according to claim 19, comprising a collar formed in the distal end of the skirt portion of the outside guide member, the collar inclining to the outside in the distal end direction of the outside guide member.

21. A transfer needle assembly according to claim 18, comprising a collar formed in the distal end of the skirt portion of the outside guide member, the collar inclining to the outside in the distal end direction of the outside guide member.

22. A transfer needle assembly according to claim 1, comprising a plurality of vertical ribs provided in an inner wall of the inside guide member.

23. A transfer needle assembly according to claim 22, comprising a collar formed in the distal end of the skirt portion of the outside guide member, the collar inclining to the outside in the distal end direction of the outside guide member.

24. A transfer needle assembly according to claim 1, comprising a collar formed in the distal end of the skirt portion of the outside guide member, the collar inclining to the outside in the distal end direction of the outside guide member.

25. A transfer needle assembly comprising:

a cap-like outside guide member having a top surface and a skirt portion;

a tubular inside guide member that is positioned in the outside guide member; and a puncture member which passes through the top surface of the outside guide member and has a proximal end and a distal end, wherein:

the puncture member is a tubular member having at its proximal end a tip fitting portion for fitting a syringe tip and having at its distal end a puncture needle;

the puncture needle is provided with a liquid passage;

the liquid passage communicates with the tip fitting portion;

the inside guide member is capable of sliding along an inner wall of the skirt portion of the outside guide member from a position where a distal end of the puncture needle is receded in an inside of the inside guide member, to a position where the distal end of the puncture needle projects outside of the inside guide member;

in the position where the distal end off the puncture needle is receded in the inside of the inside guide member, the outside guide member and the inside guide member are releasably engaged with each other so as to be incapable of sliding; and the engagement between the outside guide member and the inside guide member is releasable by insertion of a mouth portion of a vial into the inside guide member;

wherein the skirt portion of the outside guide member includes:

an annular projection provided in an inner wall of a distal end of the skirt portion;

a plurality of slits extending in an axial direction of the outside guide member formed in a portion of the skirt portion on a proximal end side with respect to the annular projection; and a plurality of flexible engaging claws formed between pairs of the plurality of slits, the plurality of flexible engaging claws inclining toward an inside of the outside guide member in a distal end direction, wherein a proximal end side of the inside guide member includes:

an annular projection provided in an outer wall of a proximal end;

a plurality of slits extending in an axial direction of the inside guide member formed in a proximal end portion of the inside guide member corresponding to the plurality of engaging claws; and a plurality of flexible pushing claws formed between pairs of the plurality of slits, the plurality of flexible pushing claws inclining toward an inside of the inside guide member in a proximal end direction, and wherein, at the position where the distal end of the puncture needle is receded in the inside of the inside guide member, the engaging claws and the proximal end of the inside guide member are engaged with each other and the annular projection of the outside guide member and the annular projection of the inside guide member are engaged with each other, and by inserting the mouth portion of the vial into the inside guide member, the pushing claws push the engaging claws to the outside, causing the engaging claws to deform and release the engagement between the outside guide member and the inside guide member.

* * * * *